United States Patent [19]
Takamura et al.

[11] Patent Number: 5,035,832
[45] Date of Patent: Jul. 30, 1991

[54] MILD LIQUID AQUEOUS DETERGENT COMPOSITIONS CONTAINING AN ALKYLSACCHARIDE SURFACE ACTIVE AGENT AND A SILICONE DERIVATIVE

[75] Inventors: Hiromi Takamura, Tokyo; Jun Kamegai, Ichikawa; Hajime Hirota, Tokyo, all of Japan

[73] Assignee: KAO Corporation, Tokyo, Japan

[21] Appl. No.: 521,845

[22] Filed: May 10, 1990

[30] Foreign Application Priority Data

May 17, 1989 [JP] Japan ................... 1-123694

[51] Int. Cl.$^5$ .......................... C11D 1/82; C11D 3/22
[52] U.S. Cl. .............................. 252/174.15; 252/173; 252/174.17; 252/DIG. 5; 252/DIG. 13; 252/DIG. 14
[58] Field of Search ...................... 252/174.15, 174.17, 252/DIG. 5, DIG. 13, 173, DIG. 14

[56] References Cited

U.S. PATENT DOCUMENTS 2,826,551  3/1958  Geen ................................. 252/89
4,668,422  5/1987  Malik et al. ..................... 252/174.17
4,704,272  11/1987 Oh et al. ............................. 424/70
4,728,457  3/1988  Fieler et al. ..................... 252/174.15
4,788,006  11/1988 Bolich, Jr. et al. ................. 252/550

OTHER PUBLICATIONS

"Encycopedia of Polymers & Th ickeners for Cosmetics" Cosmetics & Toiletries, vol. 103 (Dec. 1988), pp 99, 115–119, 121, 127–129.

Primary Examiner—Paul Lieberman
Assistant Examiner—A. Beadles-Hay
Attorney, Agent, or Firm—Oblon, Spivak, McClelland, Maier & Neustadt

[57] ABSTRACT

A detergent composition comprising an alkylsaccharide surface active agent and a silicone derivative is disclosed. The composition can produce fine, slippery, creamy foam, imparts the least irritation to the skin and hair, a tense, slippery feeling to the hair, and a light, refreshing feeling to the skin. The detergent composition thus can be favorably used as a shampoo and a body shampoo.

7 Claims, No Drawings

MILD LIQUID AQUEOUS DETERGENT COMPOSITIONS CONTAINING AN ALKYLSACCHARIDE SURFACE ACTIVE AGENT AND A SILICONE DERIVATIVE

BACKGROUND OF THE INVENTION

1. Field of the Invention

This invention relates to a detergent composition which can favorably be used as a shampoo, skin cleanser, and the like, and more particularly, to a detergent composition which can produce fine, slippery, creamy foam. It imparts the least irritation to the skin and hair, and, at the same time, a tense, slippery feeling to the hair, and a light, smooth feeling to the skin.

2. Description of the Background Art

Conventional detergents such as shampoos contain anionic surface active agents, e.g. alkyl sulfate, polyoxyethylene alkyl sulfate, as their major components. Such anionic surface active agents, however, are known to damage the skin and the hair, since the hair and horny layers to be washed are made up of keratinous protein which are liable to be denatured by anionic surface active agents.

Nonionic type shampoos has been introduced as a product which cause less damages to the hair (Japanese Patent Application Laid-open No. 13609/1978). Polyoxyethylene sorbitan ester (TWEEN) and alkyl glycoside are proposed as nonionic surface active agents used in the shampoo. The foam produced by nonionic surface active agents, however, is not necessarily sufficient in terms of both the amount and the quality. That is to say, the foam is coarse and less slippery. Alkylsaccharides are known as nonionic surfactants having better foaming capability. The foam, however, does not satisfy the basic quality requirements, imparting a creaky feeling upon use. Alkylsaccharides thus are not necessarily satisfactory surface active agents for shampoos and body shampoos.

The purpose of the present invention is to provide, with due consideration to the drawbacks of such conventional shampoos and the like, a detergent composition which imparts the least damages to the skin and produces fine, smooth, slippery foam.

SUMMARY OF THE INVENTION

Extensive studies undertaken by the present inventors in order to accomplish the above purpose revealed that the combined use of an alkylsaccharide surface active agent which is a nonionic surface active agent and a silicone derivative produced an improved detergent composition which can produce favorable fine foam, imparts the least irritation to the skin and the hair, and gives a light, tense, slippery feeling to the skin and the hair without a creaky feeling.

Accordingly, an object of this invention is to provide a detergent composition comprising an alkylsaccharide surface active agent and a silicone derivative.

Other and further objects, features, and advantages of the invention will appear more fully from the following description.

DETAILED DESCRIPTION OF THE INVENTION AND PREFERRED EMBODIMENTS

A typical alkylsaccharide surface active agent which can be used in the present invention is that represented by following formula (I), $$R_1-O-(R_2O)_t-(G)_p \qquad (I)$$

wherein $R_1$ is a linear or branched alkyl, alkenyl, or alkylphenyl group having 6–18 carbon atoms, $R_2$ is an alkylene group having 2–4 carbon atoms, G is a reduced saccharide residue having 5–6 carbon atoms, t is a value of 0–10, and p is a value of 1–10.

Among alkylsaccharides represented by formula (I), those having an alkyl group of $C_{6-18}$, especially of $C_{8-12}$, for $R_1$, such as octyl, decyl, lauryl, or the like, are preferable. t in formula (I), which indicates the condensation degree of alkyleneoxide, is a value of 0–10, preferably 0–4, and most preferably 0. G in formula (I), which is the basic unit of the hydrophillic portion of the alkylsaccharide, is a reduced saccharide residue having 5–6 carbon atoms. Glucose, galactose, and fructose are preferable reduced saccharide residues. The average polymerization degree of saccharide indicated by p in formula (I) is 1–10, and preferably 1–4. It is desirable to determine the polymerization degree considering the characteristics derived from the hydrophobic group $R_1$. For example, when $R_1$ is a hydrophobic group having an average bon atom content of 8–11, a preferable value of p is 1–1.4, while for $R_1$ with an average carbon atom content of 12–14, the p value of 1.5–4.0 is preferable. Such a polymerization degree of saccharide can be determined by the proton NMR method.

There is no specific restrictions as to the amount of alkylsaccharides to be incorporated into the composition of the present invention, although a preferable amount is 1–50%, with the especially preferable amount being 5–30%.

Following compounds are given as examples of silicone derivatives which can be used in conjunction with the alkylsaccharide in this invention.

(1) Dimethylpolysiloxanes represented by formula (II)

$$(CH_3)_3SiO[(CH_3)_2SiO]_{n1}Si(CH_3)_3 \qquad (II)$$

wherein $n1$ is an integer of 3 or more.

Dimethylpolysiloxane commercially available under the trademark of KF96 (product of Shin-etsu Chemical Co., Ltd.) is given as a typical example of the compound of formula (II).

(2) Methylphenylpolysiloxane represented by formula (III)

$$(CH_3)_3SiO[(CH_3)_2SiO]_a[\underset{\underset{C_6H_5}{|}}{\overset{\overset{CH_3}{|}}{Si}O}]_b[(C_6H_5)_2SiO]_cSi(CH_3)_3 \qquad (III)$$

wherein a, b, and c are numbers of which the sum is 1–550, provided that when b is 0, c is other than 0, and when c is 0, b is other than 0.

Methylphenylpolysiloxanes of formula (III) are widely known compounds, and are commercially available, for example under the trademark of KF50 (a product of Shin-etsu Chemical Co., Ltd.).

(3) Amino-modified silicone represented by formula (IV)

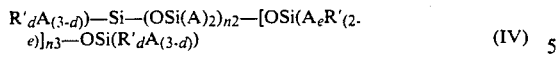

wherein R is a hydrogen, phenyl group, hydroxyl group, or alkyl group having 1-8 carbon atoms, d is 0 or an integer of 1-3, and e indicates 0 or 1, n2 is 0 or an integer of 1-1,999, n3 is an integer of 1-2,000, provided that (n2 +n3) is 1-2,000, and R' is a group $—C_fH_{2f}L$; wherein f denotes an integer of 2-8, and L is a group selected from (a)-(f):

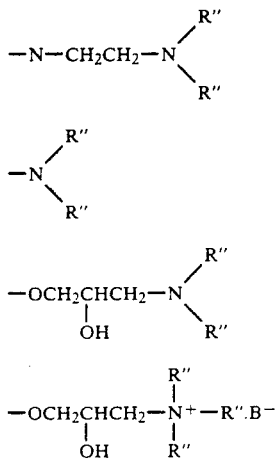

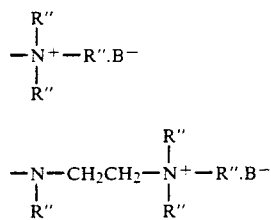

wherein R" is a hydrogen, phenyl group, benzyl group, or alkyl group having 1-20 carbon atoms, $B^-$ is $Cl^-$, $Br^-$, $F^-$, $I^-$.

As an amino-modified silicone of formula (IV), products commercial available under the trademarks SF8417 and DC536 (manufactured by Toray Silicone Co.), an aminoalkyl silicone emulsion SM8702C (trademark, manufactured by Toray Silicone Co.), or the like can be used.

(4) Fatty acid-modified silicone represented by formula (V)

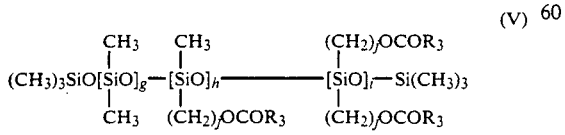

wherein g, h, and i are individually a number of 1-350, j is a number of 0-10, and $R_3$ is an alkyl group having carbon atoms of 9-21.

(5) Alcohol-modified silicone represented by formula (VI-1) or (VI-2)

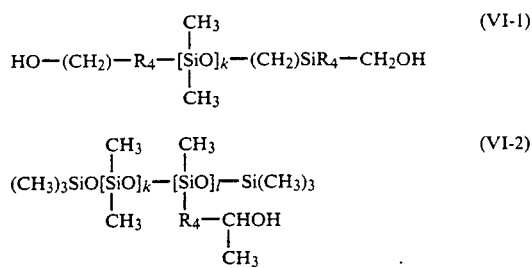

wherein k and l individually indicates a number of 1-500, preferably of 1-200, and $R_4$ represents a group $C_{n4}H_{2n4}$, wherein n4 is a number of 0-4.

(6) Fatty acid alcohol-modified silicone represented by formula (VII)

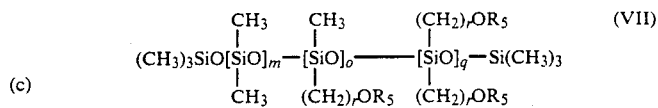

wherein m, o, and q are numbers of which the sum is 1-300, provided that r is 0-5, and $R_5$ represents a group $C_{n5}H_{2n5+1}$, wherein n5 is a number of 4-22.

(7) Polyether-modified silicone represented by formula (VIII-1) or (VIII-2)

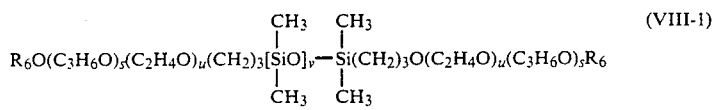

wherein s is a number of 0-35, us is a number of 1-45, v is a number of 0-400, and $R_6$ represents a group $C_{n6}H_{2n6+1}$, wherein n6 is a number of 1-4

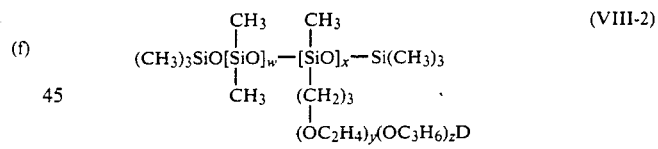

wherein w is a number of 2-110, and preferably of 20-80; x is a number of 1-50, and preferably of 3-30; y is a number of 0-50, and preferably of 5-30; z is a number of 0-50, and preferably of 0-35; and D represents an alkyl group having 1-12 carbon atom or a group $OC_{n7}H_{2n7+1}$, wherein n7 is a number of 0-6.

Silicone ether copolymers represented by formula (VIII-1) and (VIII-2) are well known and commercially available under the trademarks of KF351, KF352 (both manufactured by Shin-etsu Chemical Co., Ltd.), and the like. They are suitable for use in the present invention.

(8) Epoxy-modified silicone represented by formula (IX)

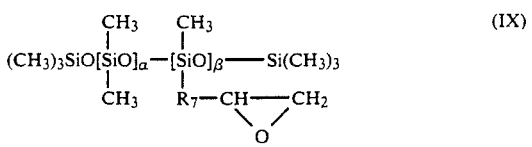

wherein $\alpha$ is a number of 1-500, and preferably of 1-250; $\beta$ is a number of 1-50, and preferably of 1-30; and $R_7$ represents an alkylene group having 1-3 carbon atoms.

(9) Fluorine-modified silicone represented by formula (X)

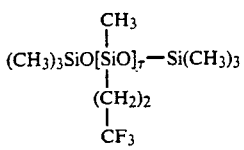

wherein $\tau$ is a number of 1-400, and preferably of 1-250.

(10) Cyclic silicone represented by formula (XI)

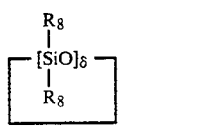

wherein $\delta$ is a number of 3-8 and $R_8$ represents an alkyl group having 1-3 carbon atoms.

(11) Alkyl-modified silicone represented by formula (XII-1) or (XII-2)

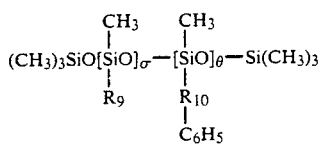

wherein $\theta$ and $\sigma$ are individually a number of 1-500, and preferably of 1-200, $R_9$ represents an alkyl group having 2-18 carbon atoms, and $R_{10}$ represents a group $C_{n8}H_{2n8}$, wherein n8 is a number of 0-4.

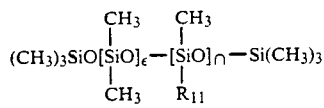

wherein $\epsilon$ and $\cap$ are individually a number of 1-500, and preferably of 1-200, $R_{11}$ is an alkyl group having 10-16 carbon atoms.

In preparing the detergent composition of the present invention using these silicone derivatives together with alkylsaccharide surface active agents, a suitable silicone derivative can be selected depending on the feeling which the composition intends to give to its users, such as soft finish upon use. More specifically, favorable slippery foam and excellent finish can be obtained when (1) methylpolysiloxane, (2) methylphenylpolysiloxane, (3) amino-modified silicone, (7) polyether-modified silicone, or (10) cyclic silicone is used as a silicone derivative. Especially good results are obtained when a silicone derivative (1), (3), (7), or (10) is used. When the composition is to be used with the skin or the hair, (1) methylpolysiloxane, (3) amino-modified silicone, (7) polyether-modified silicone, or (10) cyclic silicone will give superior tensity to the hair and a superb light feeling to the skin. In this respect, most preferable silicone derivatives are (1), (3), and (7).

Regarding to (1) methylpolysiloxane compounds, n1 in formula (II) can be selected from the range of 0 to 9,000 depending on the required feeling of finish. If light finish is desired, n1 may be between 100 and 1,000. If, on the other hand, a light feeling to the skin and a tense, fast feeling to the hair are intended, n1 greater than 2,000, preferably greater than 4,000, is desired. With respect to amino-modified silicone (3), a compound described as "Amodimethicone" in the American CTFA dictionary is particularly preferable. This compound has the chemical structure of formula (IV) and in the formula d=0, e=1, f=3, A is hydroxyl and methyl groups, and L is $-NHCN_2CH_2NH_2$.

The amount of silicone derivatives to be incorporated into the detergent composition of the present invention is 0.1-10% by weight, with the especially preferable amount being 0.1-5% by weight.

The detergent composition of the present invention can be prepared by mixing an alkylsaccharide surface active agent and a silicone derivative by a conventional method. Besides these two essential components, optional components which are appropriate to the types and intended use of the product can be added. Such optional components include, for example, anionic surface active agents of sulfonate-, sulfate-, carboxylate-, and phosphate type; nonionic surface active agents, and amphoteric surface active agents. In addition, such components as viscosity adjustment agents, UV absorbers, preservatives, antiseptics, antidandruffs, perfumes, coloring agents, and the like can be added depending on the intended use of the composition. Furthermore, in order to promote a stable incorporation of silicone derivatives into the composition, solubilizing adjuvants such as ethanol, isopropanol, and the like, or polymer-type viscosity increasing agents such as cationized guarh-gum and the like can be added.

The combined use of the alkylsaccharide surface active agent and the silicone derivative in the present invention provides a detergent composition which can produce fine creamy foam, imparts the least irritation to the skin and the hair, and gives a tense, slippery feeling to the hair and a light slippery feeling without a creaky feeling to the skin.

Other features of the invention will become apparent in the course of the following description of the exemplary embodiments which are given for illustration of the invention and are not intended to be limiting thereof.

EXAMPLES

Sensory evaluations of the compositions prepared in the following examples were carried out according to the following manner.

Feeling of foam

Sample compositions, each 1 g, were applied to a bundle of hair (weight: 20 g, length: 20 cm) of a Japanese. Feeling of the foam through washing and rinsing were evaluated by 8 expert panelists according to the following standard.

AAA: Foam was fine and creamy.
BBB: Foam was fine but not felt creamy.
CCC: Foam was coarse and not creamy.

Feeling to the touch of the hair and the skin

The same bundle of hair as above was washed with 1 g of liquid detergent compositions and dried, and subjected to the sensory evaluation by 8 expert panelists. Feeling to the touch of the skin was evaluated by foaming 1 g of the sample detergent composition with wet hands and drying the hands with towel.

AAA: Hair felt slippery and tense. The skin felt light and refreshing.
BBB: Hair felt slightly slippery and tense. The skin felt slightly light and refreshing.
CCC Hair was creaky and the skin felt sticky.

EXAMPLE 1

Detergent compositions were prepared according to the formulations listed in Table 1, and feelings of the foam and feelings to the touch of the skin and hair were evaluated. The results are given in the same table.

TABLE 1

|  | Invention Composition | | | | | | | | | Comparative Composition | |
|---|---|---|---|---|---|---|---|---|---|---|---|
|  | 1 | 2 | 3 | 4 | 5 | 6 | 7 | 8 | 9 | 1 | 2 |
| Decylpolyglucoside $C_{10}$—$Glc_{1.3}$ * 1 | 25% | 25% | 25% | 25% | — | — | — | — | 25% | 25% | — |
| Laurylpolyglucoside $C_{12}$—$Glc_{2.5}$ * 2 | — | — | — | — | 25% | 25% | 25% | 25% | — | — | 25% |
| Methylpolysiloxane * 3 | 2% | — | — | — | 2% | — | — | — | — | — | — |
| Methylphenylpolysiloxane * 4 | — | 2% | — | — | — | 2% | — | — | — | — | — |
| Polyether-modified siloxane * 5 | — | — | 2% | — | — | — | 2% | — | — | — | — |
| Amino-modified siloxane * 6 | — | — | — | 2% | — | — | — | 2% | — | — | — |
| Cyclic silicone * 7 | — | — | — | — | — | — | — | — | 2% | — | — |
| Refined water | 73% | 73% | 73% | 73% | 73% | 73% | 73% | 73% | 73% | 73% | 73% |
| Feeling of foam | AAA | AAA | AAA | AAA | AAA | AAA | AAA | AAA | AAA | CCC | BBB |
| Feeling to the touch to the skin and hair | AAA | AAA | AAA | AAA | AAA | AAA | AAA | AAA | AAA | BBB | BBB |

* 1 $C_{10}$: Decyl group, Glc: Glucose residue
* 2 $C_{12}$: Lauryl group, Glc: Glucose residue
* 3 Silicone KF96 (30,000 cs); product of Shin-etsu Chemical Co.
* 4 Silicone KF56; product of Shin-etsu Chemical Co.
* 5 Silicone KF351A; product of Shin-etsu Chemical Co.
* 6 Silicone SF8417; product of Toray Co., Ltd.
* 7 Silicone KF9956; product of Shin-etsu Chemical Co.

EXAMPLE 2

| Shampoo Composition (Formulation) | |
|---|---|
| (1) Decylpolyglucoside $C_{10}$—O—$Glc_{1.3}$ | 20% (by weight) |
| (2) Aminoalkylpolysiloxane * 8 | 3% |
| (3) Laurylamine oxide * 9 | 1% |
| (4) Coconut oil diethanolamide * 10 | 1% |
| (5) Polyethyleneglycol distearate (190 EO) * 11 | 1% |
| (6) Ethyleneglycol distearate | 2% |
| (7) Butylhydroxytolunene | 0.2% |
| (8) Coloring agent | Small amount |
| (9) Perfume | Small amount |
| (10) Refined water | Balance |

* 8 Silicone SM8702, product of Toray Silicone Co., Ltd.
* 9 Anhitol 20N, product of Kao Corp.
* 10 Amisol L02, product of Kawaken Fine Chemical Co.
* 11 Emanone 2399R, product of Kao Corp.

Method of preparation

Components (1)–(7) were homogeneously dispersed into refined water (10). After cooling, components (8) and (9) were added to the dispersion to produce a shampoo composition.

The shampoo composition produced fine creamy foam and gave a tense, glossy finish after washing.

EXAMPLE 3

| Shampoo Composition (Formulation) | |
|---|---|
| (1) Laurylpolyglucoside $C_{12}$—O—$Glc_{2.3}$ | 20% (by weight) |
| (2) Methylpolysiloxane * 3 | 3% |
| (3) Laurylamine oxide * 9 | 1% |
| (4) Cationized cellulose * 12 | 0.5% |
| (5) Monoalkylphosphate triethanolamine salt | 2% |
| (6) Ethyleneglycol distearate | 2% |
| (7) Octopyrrox | 0.2% |
| (8) Butylhydroxytoluene | 0.2% |
| (9) Coloring agent | Small amount |
| (10) Perfume | Small amount |
| (11) Refined water | Balance |

* 12 Polymer LR 30M, product of Union Carbide Corp.

Method of Preparation

Components (1)–(8) were homogeneously dispersed into refined water (11). After cooling, components (9) and (10) were added to the dispersion to produce a shampoo composition.

The shampoo composition produced fine creamy foam and gave a tense, glossy finish after washing.

EXAMPLE 4

| Body Shampoo Composition (Formulation) | |
|---|---|
| (1) Decylpolyglucoside $C_{10}$—O—$Glc_{1.3}$ | 20% (by weight) |
| (2) Methylpolysiloxane * 3 | 3% |
| (3) Triiethanolamine myristate | 5% |
| (4) Glycerol | 5% |
| (5) Ethyleneglycol distearate | 3% |
| (6) Zinc stearate | 0.2% |
| (7) Butylhydroxytoluene | 0.2% |
| (8) Ethylhexyl p-dimethylamino-benzoate * 13 | 0.5% |
| (9) Coloring agent | Small amount |
| (10) Perfume | Small amount |
| (11) Refined water | Balance |

* 13 Escarol 507, product of Bandike Co.

Method of Preparation

Components (1)–(8) were homogeneously dispersed into refined water (11) at 70° C. After cooling, components (9) and (10) were added to the dispersion to produce a body shampoo composition.

The body shampoo composition produced fine creamy foam and gave a light, refreshing finish after washing.

EXAMPLE 5

| Shampoo Composition (Formulation) | |
| --- | --- |
| (1) Polyoxyethylene (2EO) dodecyl-β-glucoside | 15% (by weight) |
| (2) Polyether-modified silicone (Silicone KF351A) | 3% |
| (3) Lauryldimethylamine oxide | 1% |
| (4) Coconut oil diethanolamide | 1% |
| (5) Perfume | 0.3% |
| (6) Refined water | Balance |

Method of Preparation

Components (1)–(4) were dissolved into refined water at 60° C. After cooling, component (5) was added to the solution to produce a body shampoo composition.

The shampoo composition produced fine foam and gave a refreshing feeling after washing.

Obviously, numerous modifications and variations of the present invention are possible in light of the above teachings. It is therefore to be understood that within the scope of the appended claims, the invention may be practiced otherwise than as specifically described herein.

What is claimed is:

1. A detergent composition comprising an alkylsaccharide surface active agent present in an amount of 1 to 50% and a silicone derivative present in an amount of 0.1 to 10%; wherein:

said alkylsaccharide surface active agent is a compound of the formula (I), $$R_1-(R_2O)_t-(G)_p \qquad (I)$$

wherein $R_1$ is a linear or branched alkyl, alkenyl, or alkylphenyl group having 6–18 carbon atoms, wherein $R_2$ is an alkylene group having 2–4 carbon atoms, G is a reduced saccharide residue having 5 or 6 carbon atoms, t is 0–10, and p is 1–10; and said silicon derivative is a compound selected from the group consisting of dimethylpolysiloxanes, methylphenylpolysiloxanes, amino-modified silicones, fatty acid-modified silicones, alcohol-modified silicones, fatty acid alcohol-modified silicones, polyether-modified silicones, epoxy-modified silicones, fluorine-modified silicones, cyclic silicone, and alkyl-modified silicones.

2. The composition of claim 1, wherein $R_1$ contains from 8 to 12 carbon atoms, t is from 0 to 4, and p is from 1 to 4.

3. The composition of claim 1, wherein t is 0.

4. The composition of claim 1, wherein said reduced saccharide residue is a glucose, galactose, or fructose residue.

5. The composition of claim 1, wherein $R_1$ contains from 8 to 11 carbon atoms and p is from 1 to 1.4.

6. The composition of claim 1, wherein $R_1$ contains from 12 to 14 carbon atoms and p is from 1.5 to 4.0.

7. The composition of claim 1, wherein said alkylsaccharide surface active agent is present in an amount of from 5 to 30%.

* * * * *

UNITED STATES PATENT AND TRADEMARK OFFICE
CERTIFICATE OF CORRECTION

PATENT NO. : 5,035,832

DATED : July 30, 1991

INVENTOR(S) : Hiromi Takamura et al.

It is certified that error appears in the above-identified patent and that said Letters Patent is hereby corrected as shown below: Title page;

The Foreign Application Priority Data is incorrect, should be, --May 17, 1989  [JP]  Japan ..............1-123964--.

Signed and Sealed this

Twelfth Day of January, 1993

*Attest:*

DOUGLAS B. COMER

*Attesting Officer*   Acting Commissioner of Patents and Trademarks